United States Patent [19]

Renberg et al.

[11] Patent Number: 5,842,150
[45] Date of Patent: *Nov. 24, 1998

[54] METHOD OF DETERMING THE ORGANIC CONTENT IN PULP AND PAPER MILL EFFULENTS

[75] Inventors: Lars Renberg, Västerhaninge; Anders Sparén, Göteborg, both of Sweden

[73] Assignee: Eka Chemicals AB, Bohus, Sweden

[ * ] Notice: The term of this patent shall not extend beyond the expiration date of Pat. No. 5,680,321.

[21] Appl. No.: 817,359

[22] PCT Filed: Oct. 10, 1995

[86] PCT No.: PCT/EP95/04030

§ 371 Date: Apr. 11, 1997

§ 102(e) Date: Apr. 11, 1997

[87] PCT Pub. No.: WO96/12183

PCT Pub. Date: Apr. 25, 1996

[30] Foreign Application Priority Data

Oct. 14, 1994 [SE] Sweden .................................. 9403520

[51] Int. Cl.[6] .............................. G01N 33/34; D21C 9/10
[52] U.S. Cl. ................................. 702/23; 702/25; 702/30
[58] Field of Search ..................... 364/496–499, 364/578; 162/56, 198, 49; 210/632, 745, 143; 702/23, 25, 30, 22

[56] References Cited

U.S. PATENT DOCUMENTS

| | | | |
|---|---|---|---|
| 4,743,339 | 5/1988 | Faix et al. | 162/49 |
| 5,121,337 | 6/1992 | Brown | 364/498 |
| 5,242,602 | 9/1993 | Richardson et al. | 210/745 |
| 5,368,688 | 11/1994 | Miki et al. | 162/56 |
| 5,470,480 | 11/1995 | Gray et al. | 210/632 |
| 5,680,321 | 10/1997 | Helmer et al. | 364/499 |

FOREIGN PATENT DOCUMENTS

| | | |
|---|---|---|
| 0 344 694 | 12/1989 | European Pat. Off. . |
| 0 559 305 | 9/1993 | European Pat. Off. . |
| WO 92/17642 | 10/1992 | WIPO . |
| WO 94/01769 | 1/1994 | WIPO . |

OTHER PUBLICATIONS

Interoffice memo, *Subject Analysis of Alcohol in Wine and Must*, dated Feb. 17, 1984.
*Addition of methanol to a kraft cook*, Nordic Pulp & Paper Research Journal No. 1–1994 9 (1994).
*Multivariate Data Analysis of in Situ Pulp Kinetics Using 13C CP/MAS NMR.*, Journal of Wood Chemistry and Technology, 9(2), 235–249 (1989).
*Potential Applications for near infrared spectorscopy in the pulping industry*, Paper Southern Africa –November/Dec. 1988, pp. 34–38.
*Utlosning AV Kolhydrater Under Sulfat–Kokning AV Bjork*, Stockholm, 1989, Tomas Josefsson.
*International Search Report*, dated Feb. 28, 1996.
*Water, Air & Soil Pollution*, vol. 39, 1988 pp. 75–80.
*Potential Applications for Near Infrared Spectroscopy in th Pulping Industry*, pp. 34–38, Paper Southern Africa Nov./Dec. 1988.
*Chemometrics, Analytical Chemistry*, vol. 62, No. 12 Jun. 15, 1990 pp. 84–101.

*Primary Examiner*—Melanie Kemper
*Attorney, Agent, or Firm*—Ralph J. Mancini

[57] ABSTRACT

A method, based on UV/VIS/NIR/IR (including Raman spectroscopy), is provided for the qualitative and quantitative determination of quality parameters in pulp and paper and/or the organic content in effluents from pulp and paper production, by applying chemometric methods.

16 Claims, 2 Drawing Sheets

METHOD OF DETERMING THE ORGANIC CONTENT IN PULP AND PAPER MILL EFFULENTS

This is the national stage of International Application No. PCT/EP95/04030, filed on Oct. 10, 1995.

FIELD OF THE INVENTION

The present invention is directed to a method for qualitative and quantitative determination of various parameters reflecting the pulp or paper quality and environmental impact of pulp and paper production, and more particularly to a spectroscopic method for the instantaneous and continuous analysis of the various parameters reflecting the quality of the pulp and paper as well as the environmental impact of the effluents paper, performed on the aqueous phases from the process stages in a pulp mill or paper mill.

BACKGROUND OF THE INVENTION

The main constituents of wood are cellulose, hemicellulose, lignin and extractives. The quality of pulp or paper is strongly related to its content of cellulose i.e a higher cellulose content increases the quality. Especially lignin, which is an aromatic crosslinked polymer, is an unwanted constituent in the pulp and affects the quality of the pulp negatively. In chemical pulp production the major part of the lignin is removed in the cooking process.

The remaining lignin is removed in a process, referred to as bleaching, by chemical oxidation. The bleaching process consists usually of 3–5 stages. Examples of oxidation chemicals used for bleaching are molecular chlorine, chlorine dioxide, hydrogen peroxide and ozone. Usually an alkaline extraction stage is employed between the different oxidation stages. From each bleaching stage an aqueous discharge is obtained, containing the degradation products of mainly lignin. This water soluble organic material reflects the mechanisms and removal efficiencies of the oxidation processes.

The bleached pulp is characterized by e.g. the kappa number, paper whiteness, measured as ISO-90 or similar parameters, paper strength, commonly measured as viscosity, tear index, tensile index or burst index.

The measurement of the kappa number in the aqueous phase is a relatively crude measurement of the reduction in the lignin content after each stage. According to the Technical Association of Pulp and Paper Industries (TAPPI) the kappa number reflects the relative hardness, bleachability or degree of delignification. The kappa number is defined as the degree of consumption of potassium permanganate (TAPPI Standard Method T 236 cm-85). Another, very similar and standardised method methods is SCAN-C 1:77.

The viscosity is a surrogate parameter reflecting the pulp strength and is often used instead of the more tedious determination of paper strength by tear index, tensile index and burst index.

Another important quality parameter is the whiteness or the brightness of the pulp and paper, which usually is measured as ISO-90.

The environmental impact of pulp and paper mill effluents is often assessed using parameters reflecting the organic content. Such parameters are the chemical oxygen demand (COD), the biological oxygen demand (BOD 5, BOD 7 and BOD 28), the total organic content (TOC), the colour of the effluent, adsorbable organohalogenes (AOX), suspended organic material and washing losses, the latter expressed as COD or sodium sulphate.

One major drawback with methods according to prior art of monitoring the efficiency of the bleaching process is the delay between the sampling of the bleach plant effluent and the determination of the kappa number and other conventional parameter, currently in use.

This delay may lead to important quality losses as appropriate measures are unnecessarily delayed. Another disadvantage with prior art methods are that the characteristics and distribution of this chemically very complex organic material is not very well described by these simple methods. It is obvious that there is a definite need for more convenient and relevant methods for characterising the quality of the pulp and the organic material in pulp mill effluents. The present invention has for object to offer a solution to the mentioned and similar problems, by providing a method that allows the continuous monitoring of pulp mill effluents during the pulp and paper mill process. This object is attained by the combined use of spectrometric and chemometric techniques.

According to the invention, the aqueous effluent is submitted to spectrometric analysis. However, the water-soluble organic material represents a multi-component system or a system having a high degree of background interferences which greatly complicate the problem of spectrometric analysis.

The use of multivariate data analysis in the characterisation of multi-component systems is presently a field of development. Applied generally to the field of chemistry, and particularly to the field of analytical chemistry, those several statistical methods are also termed chemometric methods, forming the discipline of chemometrics. The technique of chemometrics is more fully explained in S. D. Brown, "Chemometrics", Anal. Chem. 62, 84R–101R (1990), which by reference is incorporated herein in its entirety.

Brown et al, in the U.S. Pat. No. 5,121,337 (1990) disclose a method, based on multivariate data analysis, for correcting spectral data for data due to the spectral measurement process itself and estimating unknown property and/or composition data of a sample using such method.

Richardson et al, in U.S. Pat. No. 5,242,602 (1992) disclose a method for simultaneously analyzing the concentration of performance indicators in aqueous system by determining an absorbance or emission spectrum in a wavelength range of 200 to 2500 nm and applying chemometric algorithms to the absorbance or emission spectrum. Said performance indicators are selected from scale inhibitors, corrosion inhibitors, lubricants, metal working fluids, pH regulators, dispersants, defoaming agents, sequestrants, biocides, detackifiers, and precipitating agents. The concentrations of the performance indicators determined by the chemometric algorithms are compared to predefined ranges for the respective performance indicators.

However, the combination of simultaneously measuring several wavelengths of a liquid sample and applying chemometric techniques has been described and applied as a general technique. For example, Hewlett-Packard, a commercial company which is manufacturing chemical-analytical instrument, discusses the importance of chemometrical methods for multicomponent analysis using multiwavelength spectroscopy in its booklet "The diode-array advantage in UV/Visible Spectroscopy" (Hewlett Packard Co, publication no.12-5954-8912,1988).

SUMMARY OF THE INVENTION

None of the above mentioned authors suggests how to solve the problem of the qualitative and quantitative determination of the various parameters related to pulp and paper production such as the lignin content reflected in the kappa number; the parameters reflecting the paper strength such as the viscocity, tear index, tensile index and burst index; brightness measured as ISO-90; or the parameters reflecting the organic content in the effluents, such as chemical oxygen demand (COD), washing losses expressed as COD or sodium sulphate, the total organic content (TOC); and the biological oxygen demand (BOD 5, BOD 7 and BOD 28); colour, suspended solid material, adsorbable organohalogenes (AOX), washing losses expressed as COD or sodium sulphate in a way permitting the continuous monitoring of this parameters. This, however, is the object of the present invention, which provides a reliable and precise way of monitoring the content of organic material or parameters reflecting the change in quality of the pulp or paper by a rapid chemical analysis coupled with multivariate data analysis using the technique of chemometrics.

DETAILED DESCRIPTION OF THE INVENTION

Figure 1:
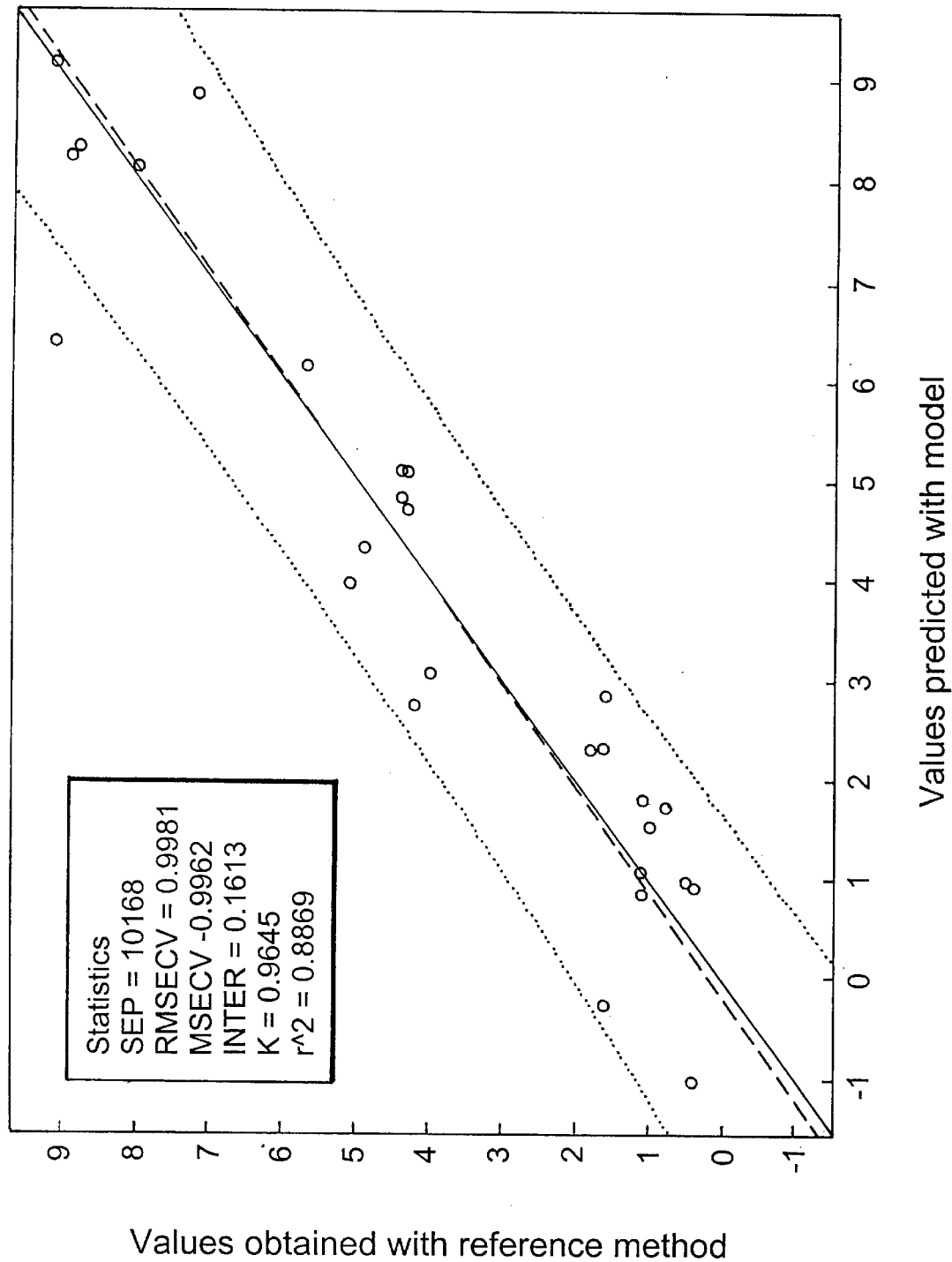
FIG. 1 shows the prediction of kappa number using a PLS model with 7 principal components.

One object of the invention is to provide a method for the estimation of the difference in kappa number in pulp mill effluents before and after one or several process stages by measuring the organic content in the aqueous phase.

It is another object of the invention to provide a method for the estimation of the difference in paper strength, measured as the viscosity value, tear index, tensile index or burst index, before and after a process stage by measuring the organic content in the aqueous phase in pulp mill effluents.

Yet another object is the estimation of the difference in paper whiteness or brightness measured as ISO-90 or similar parameters before and after a process stage by measuring the organic content in the aqueous phase.

The invention also comprises methods for the direct and instantaneous determination of chemical oxygen demand (COD), wash losses defined as COD or sodium sulphate, total organic carbon content (TOC), biological oxygen demand e.g. BOD 5, BOD 7, and BOD 28 as well as adsorbable organic halogenates (AOX), suspended solid material and colour in the aqueous phase in the pulp mill effluents. The invention also includes the determination of groups of chemically similar compounds, e.g. extractives, lignin residues and carbohydrates.

The above objects of the invention are obtained by a method of measurement of organic material in the aqueous phase of pulp and paper mill effluent by analysing the ultraviolet, visible, near-infrared and/or infrared (incl. Raman spectroscopy) spectrum of the paper/pulp in the process line in a wavelength range within 180 nm to 400 $\mu$m and applying chemometric evaluation of the spectrum to calculate the difference in quality parameters, e.g. kappa number, and direct determination of organic content, e.g. COD.

According to the invention it has now, by an extensive development work, been shown that it is possible to directly and continuously detect the absorption, transmittance or reflectance spectra in the above defined parameters and particulary the kappa number in the pulp and/or COD in pulp mill effluent using a UV/VIS/NIR/IR (including Raman spectroscopy) spectrometer and, by the use of absorbance or transmittance values at discrete wavelengths from these spectra, calculate the above defined parameters, especially the kappa number, the difference in paper strength measured as viscosity, tear index, tensile index, burst index or similar parameters; the difference in paper whiteness or brightness measured as ISO-90 or similar parameters, before and after a process stage. Further objects are the direct determination of the chemical oxygen demand (COD), wash losses expressed as COD or sodium sulphate, total organic content (TOC), as well as the biological oxygen demand (BOD 5, BOD 7, and BOD 28), adsorbable organic halogenates (AOX), suspended solid material and colour. Also the direct determination of chemically similar compounds can be carried out. Examples of such groups are extractives, lignin residues and carbohydrates.

The terminology pulp used herein refers not only to bleached pulp and/or paper, but also to unbleached or partially bleached mechanical or chemical pulp.

Technically, the spectrometric analysis can be performed by on-line, in-line or at-line detection and carried out as a continuous monitoring, by use of an on-line, in-line or at-line optical fibre probe, or by taking individual samples for separate analysis. In all cases, absorption, transmittance or reflectance spectra are subject to further data treatment using values from several discrete wavelengths from each particular spectrum.

The spectral information reflects a variety of properties of the organic content. Depending on the parameter of interest relevant and selected spectral information is correlated to the specific parameter.

An example of such a technique is the use of a device, placed at a distance from the process, containing a light source, detector, electronic components and other necessary components to transmit a signal through an optical fibre to the sample, where the light is transmitted through or reflected on or partly through the sample. The resulting signals are returned to the detector in an accompanying optical fibre cable, and recorded.

In the spectrometer, the light is converted into an electric signal which is then conveyed to a computer where the spectrum of a previously stored reference scan can be related to, e.g. subtracted from, the sample spectrum and a reference corrected spectrum is calculated.

Another example is by manually or automatically taking samples at relevant time intervals and submitting the samples to analysis in an analytical instrument, containing the light source, detector, electronic components and other necessary components. The absorption, transmittance or reflectance spectra are then subjected to further data treatment, using values from several discrete wavelengths from each particular spectrum.

It is preferred that the detector has a measuring interval of at the most 10 nm, preferably 2 nm, and most preferably 1 nm or less. The detection is performed in the UV/VIS/NIR/IR (including Raman spectroscopy) wavelength range of 180 nm to 400 $\mu$m.

This can be accomplished by the use of a scanning instrument, a diode array instrument, a Fourier transform instrument or any other similar equipment, known to the man skilled in the art.

An evaluation of wavelengths which contain absorption, transmittance or reflectance provides features relevant for the analysis. By the application of chemometrical methods to the obtained spectra it is then possible to ignore wavelengths which do not contain information that contribute to the analysis, even though the measurement will include information from the entire wavelength range.

The determination and control of e.g. the reduction in kappa number of paper in pulp and/or paper by use of the spectrometric measurements comprise two main steps, the first of which being the development of a calibration model, involving the substeps of development of learning sets; data processing; and data analysis, by the use of pulp and/or paper samples of known kappa numbers. The second main step is the spectrometric analysis of the sample of the unknown kappa number, spectral data processing, optionally followed by data analysis; and application of the calibration model, developed in the first main step, to the thereby obtained data.

(I) DEVELOPMENT OF A CALIBRATION MODEL

The kappa number is measured in the traditional way (TAPPI T 236 cm-85 (1984) or SCAN-C 1:77) for a number of pulp samples before and after a process stage. The difference of the kappa number, before and after the process stage, is then used in the development of a calibration model wherein the three substeps discussed below are applied to the registered absorption, reflectance or emission spectra of said samples.

(I.a) Development of Learning Sets

Model learning sets consist of a large number of absorption, transmittance or reflectance spectra from the samples with known kappa number characteristics, that preferably should be representative of the production line. The learning sets are used in the chemometric algorithms to calculate the resulting model parameters.

(I.b) Data Processing

To reduce noise and adjust for base line drift the spectral raw data should be processed. This processing may also reveal hidden information, such as identity of apparently dissimilar spectra or non-identity of apparently very similar spectra.

Moreover, the assumptions leading to Beer's law (stating that, for a given absorption coefficient and length of the optical path in the absorptive media, the total amount of light absorbed is proportional to the molecular concentration of the sample) are not always fulfilled in the complex system that the pulp mill effluent sample constitutes. This is due to a number of factors, such as the high concentrations, often found in industrial samples. Another complication factor is light scattering variations, depending on particles in the sample.

Various theories have been developed to overcome this problem and the most used are: the Kubelka-Munk transformation (P. Kubelka, F. Munk, Z. Tech. Physik 12, 593 (1931)), which takes account of absorption and scatter; and the Multiplicative Scatter Correction (P. Geladi, D. MacDougall, H. Martens, Appl. Spect. 39, 491–500 (1985)) where each spectrum is 'corrected' in both offset and slope by comparing it to an 'ideal' spectrum (the mean spectrum).

The Kubelka-Munk transform is according to Eq. 1:

$$A_{ik} = \frac{(1 - R_{ik})^2}{2R_{ik}} \quad (1)$$

where $R_{ik}$ is the apparent absorbance at the wavelength k, $A_{ik}$ is the transformed absorbance at the wavelength k, and the index i represents the sample spectra available.

The Multiplicative Scatter Correction (MSC) is according to Eq. 2:

$$A_{ik} = \frac{R_{ik} - \hat{a}_i}{\hat{b}_i} \quad (2)$$

where $A_{ik}$, $R_{ik}$, i and k have the same meanings as above, $a_i$ is the least squares estimation of the intercept parameter, and $b_i$ is the least squares estimation of the slope parameter. Another way of linearising the spectral data also is by use of derivatives, e.g. up to the fourth order derivatives (A. Savitzky, M. J. E. Golay, Anal. Chem. 36, 1627–1639 (1964)). The derivative of the spectrum results in a transformed spectrum, consisting only of the relative changes between the adjacent wavelengths, and it has been shown that the peak intensities of derived spectra tend to be more linear with concentration (T. C. O'Haver, T. Begley, Anal. Chem. 53, 1876 (1981)).

Linearisation can also be accomplished by use of the Fourier transformation, or by use of the Standard Normal Variate transformation as disclosed in R. J. Barnes, M. S. Dhanoa and S. J. Lister, Appl. Spectrosc., Vol. 43, number 5, pp. 772–777 (1989).

(I.c) Data Analysis

Data analysis using chemometric techniques then allows the calibration model to be developed. There are several chemometric techniques which can be used, such as Principal Component Analysis (PCA), Partial Least Squares Regression (PLS), Principal Components Regression (PCR), Multilinear Regression Analysis (MLR) and Discriminant Analysis. The preferred chemometric technique according to the invention is the PLS method.

(I.c.1) Principal Component Analysis (PCA)

By PCA, a set of correlated variables is compressed into a smaller set of uncorrelated variables. This transformation consists of a rotation of the coordinate system, resulting in the alignment of information on a fewer number of axes than in the original arrangement. Hereby, the variables that are highly correlated with one another will be treated as a single entity. By using PCA, it thus will be possible to obtain a small set of uncorrelated variables still representing most of the information which was present in the original set of variables, but being far easier to use in models. In general, 2 to 15 principal components will account for 85% to 98% of the variance of the variables. Another embodiment includes the transformation of spectral data into principal components (with or without data processing) and thus monitoring the principal components as function of time and relating these values to parameters commonly used for process control.

(I.c.2) Partial Least Squares Regression (PLS)

PLS is a modelling and computational method by which quantitative relations can be established between blocks of variables, e.g. a block of descriptor data (spectrum) for a series of samples and a block of response data measured on these samples. By the quantitative relation between the blocks, it is possible to enter spectral data for a new sample to the descriptor block and make predictions of the expected responses. One great advantage of the method is that the results can be evaluated graphically, by different plots. In most cases, visual interpretations of the plot are sufficient to obtain a good understanding of different relations between the variables. The method is based upon projections, similar to PCA. The PLS method is disclosed in detail in Carlsson R., Design and optimization in organic synthesis, B. G. M. Vandeginste, O. M. Kvalheim, Eds., Data handling in science and technology, (Elsevier, 1992), vol.8.

(I.c.3) Principal Components Regression (PCR)

PCR is closely related to PCA and PLS. As in PCA, each object in the descriptor block is projected onto a lower dimensional space yielding in scores and loadings. The scores are then regressed against the response block in a least squares procedure leading to a regression model which can be used to predict unknown samples. The same model statistics as in PLS and PCA can be used to validate the model.

For an exellent tutorial in PCA, PLS and PCR, see P. Geladi et al in "Partial Least-Squares Regression: A Tutorial" in Anal. Chim. Acta, 185, 1–32 (1986), which is incorporated herein by reference in its entirety.

(I.c.4) Multilinear Regression Analysis (MLR)

By MLR, the best fitting plane for the kappa number as a function of the spectra is defined, using least squares techniques to define each boundary of the plane. This plane is then used to recognize and assign a predicted value to an unknown kappa number. This technique is generally limited to relatively 'clean' systems where there is not a significant amount of matrix interference and, in contrast to PLS, it requires more objects than variables.

(I.c.5) Discriminant Analysis

This is a method whereby, by use of spectral data, the known kappa number values are grouped into different clusters, separated by linear decision boundaries. From its spectrum, a sample of unknown kappa number then can be matched to a cluster, and the kappa number can be assigned a value, e.g. the average value of the cluster. This is a very useful technique for quality screening, but requires a very large data base to obtain statistically significant results.

(II) DETERMINATION OF THE ORGANIC MATERIAL BY APPLICATION OF THE CALIBRATION MODEL

Once a calibration model has been developed, the determination of the unknown kappa number can be performed by registering the absorption, transmittance or reflectance spectrum, in correspondence to (I.a), from the pulp mill effluent of the unknown kappa number; processing the thereby obtained spectral raw data as according to (I.b); optionally performing a data analysis on the processed spectral data as according to (I.c); and applying the developed calibration model to the thereby obtained data.

The invention will now be illustrated by way of an example.

EXAMPLE

Multiwavelength spectroscopy, carried out on the effluents from bleaching pulp, followed by linearisation of spectral data and multivariate data evaluation (PLS algorithm) were used to determine the reduction in kappa number before and after bleaching. The organic content is expressed as kappa number reduction between two bleaching stages.

DEVELOPMENT OF A CALIBRATION MODEL (A) Development of Learning Sets

SAMPLES

The reference samples consisted of in total 55 effluents from bleaching chemical pulp, originating from different sites in the bleaching sequence, and thereby having different pHs and COD levels. The samples had been treated in different bleaching sequences and the kappa number was determined for each sample, using the TAPPI Standard Method T 236 cm-85.

UV ABSORBANCE MEASUREMENTS

The UV measurements were obtained using a Spectra Focus® Optical Scanning Detector (Spectra-Physics), equipped with a fused silica capillary with an inner diameter of 0.53 mm as the flow through cell. Measurements were made directly on the capillary, on which a 10 mm window had been obtained, by burning off the polymer coating. The samples were pumped through the capillary by means of a peristaltic pump (Gilson Minipuls 2) at a speed of 2.4 ml $min^{-1}$. A spectral operating range between 200 nm and 360 nm, in even intervals of 2 nm, was used, yielding 81 measurements at different wavelengths. Four measurements were made on each sample, and their mean spectrum was calculated and used in further evaluations. The absorbance data obtained were transferred to an IBM PS-2 7386 computer equipped with the Autolab® Software (Spectra-Physics).

(B) Data Processing

The whole spectral data matrix was used for modelling, which resulted in 81 spectral points.

LINEARISING TRANSFORMATION

Two linearising functions were tried, i.e. 2nd derivative and MSC on the original spectra. Models were built on both the original data matrix, as well as on the transformed.

(C) Data Analysis

The commercially available MATLAB software V 4.0 was used for numerical calculations. The PLS-algorithm used for modelling the relationships between the spectra and descriptors is a customised function in the PLS Toolbox, made by Barry M. Wize (free available) based on the NIPALS algorithm (H. Wold, P. Krishnaiah, Multivariate Analysis, 391 (1966)). The metod of establishing the significant number of PLS-components was crossvalidation (S. Wold, Technometrics 20, 397–405 (1978)) (Jack-knifing) with one sample left out. This procedure was repeated in an iterative manner, leaving out another sample, so that each predicted value was based on a model in which the predicted sample was not present. The values from the reference method were mean-centered and optionally scaled to unit variance prior to modelling (autoscaling or z-transform) and rescaled prior to model evaluation order to facilitate a further understanding of the invention, the following examples are presented primarily for the purpose of illustrating certain more specific details thereof. The invention is not to be limited thereby except as defined in the claims.

RESULTS

The measured vs. modelled values of the reduction in the kappa number are plotted in FIG. 1. As can be seen the deviation from the theoretical value, represented in the figure as a straight line is minimal.

Figure 2:
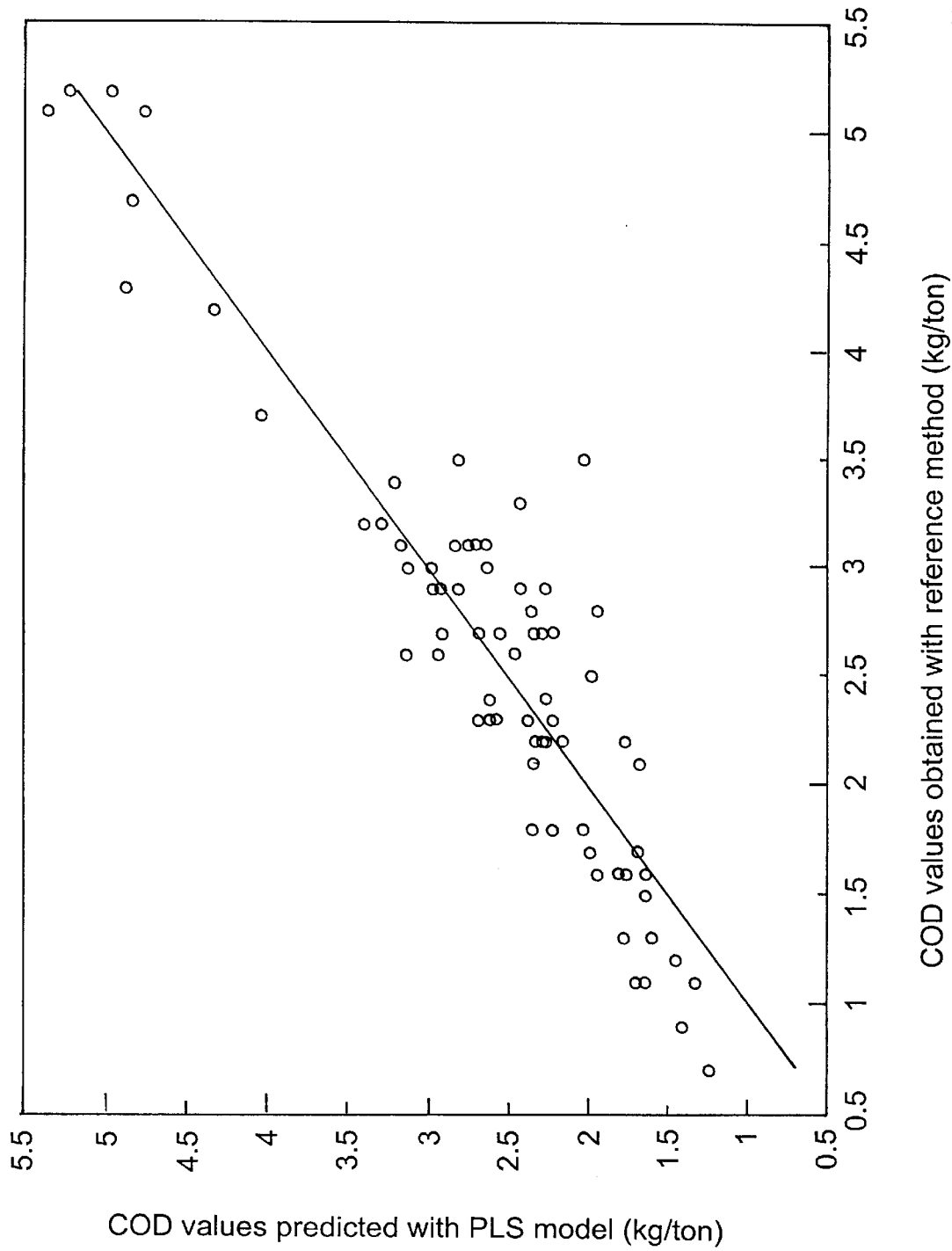
FIG. 2 shows the prediction of COD using a PLS model with 3 principal components.

In FIGS. 1 and 2 the values from the reference methods, are plotted vs. the values, calculated by the model (predicted values). Data pretreatment were multiplicative scatter correction and mean centering. Solid line denotes slope 1.0, dashed line was fitted with linear regression, while dotted lines denote the confidence limit at the 95% significance level (SEP=Standard error of prediction; RMSECV=Root mean squared error of cross validation; MSECV=Mean squared error of cross validation; INTER=intercept; K=slope; r∧2=the square of the correlation coefficient for the fitted dashed line).

FIG. 1 shows the prediction of kappa number using a PLS model with 7 principal componenents.

FIG. 2 shows the prediction of COD using a PLS model with 3 principal components.

Ideally, the slope of the line (k) and its correlation coefficient ($r^2$) should be as close to 1 as possible; while the intercept should be as close to 0 as possible. In view of the values obtained, it will be possible to realize the very good validity and precision of the model.

The advantage of the novel method of monitoring organic content in pulp or pulp mill effluent using chemometrics, should thus be readily apparent. Indeed, a wide variety of samples, originating from various pulp mills and production processes, may be analysed using the same calibration set. The invention thus provides a method whereby the monitoring of the quality of pulp and of the organic content in effluents from pulp and paper mill production process can be performed in a very rapid and precise way on any type of pulp and paper.

We claim:

1. A method for qualitative and quantitative determination of the parameters reflecting the quality of pulp or paper said method comprising:

(I) developing a calibration model by (I.a) registering absorption, transmittance or reflectance spectral raw data of reference samples of a effluent from production of a reference pulp or paper with known properties and concentrations of organic substances to develop learning sets;

(I.b) processing the spectral raw data of reference samples to reduce noise and adjust for drift and diffuse light scatter;

(I.c) performing a data analysis by applying chemometric techniques to the processed learning sets, thus calibrating the processed spectral data with actual values for parameters reflecting the quality of the reference pulp or paper, which values are determined by means of conventional analytical methods;

(II) registering absorption, transmittance or reflectance spectra of samples of an effluent from production of the pulp or paper with unknown properties and concentration of organic substances in analog with (I.a); processing the thereby obtained spectral raw data as according to (I.b); and applying the developed calibration model to the processed data in order to determine the parameters reflecting the quality of said pulp or paper.

2. The method of claim 1 wherein the differences in the product quality before and after a process stage is calculated, and this value is qualitatively and quantitatively related to the spectral information, obtained by measuring the process effluent.

3. The method of claim 2, wherein the difference in kappa number before and after a bleaching stage is calculated, and this value is quantitatively related to the selected part of the spectral information, obtained by measuring the bleach plant effluent.

4. The method of claim 2, wherein the difference in paper strength, measured as the viscosity value, before and after a bleaching stage, is calculated and the value is quantitatively related to the selected part of the spectral information, obtained by measuring the bleach plant effluent.

5. The method of claim 2, wherein the difference in paper strength, measured as tear index, tensile index, burst index and similar parameters, is calculated before and after a bleaching stage, and this value is quantitatively related to the selected part of the spectral information, obtained by measuring the bleach plant effluent.

6. The method of claim 2, wherein the difference in paper whiteness or brightness, measured as ISO-90 or similar parameters, is calculated before and after a bleaching stage, and the value is quantitatively related to the selected part of the spectral information, obtained by measuring the bleach plant effluent.

7. The method of claim 1, wherein the organic content in pulp and paper process effluents is determined, and this value is qualitatively and quantitatively related to selected parts of the spectral information, obtained from the process effluent.

8. The method of claim 7, wherein the organic content, defined as chemical oxygen demand (COD), in the aqueous effluent from pulp mill or paper mill production is determined, and the obtained COD value is quantitatively related to selected parts of the spectral information, obtained from the effluent.

9. The method of claim 7, wherein the organic content, defined as total organic carbon content (TOC), in the aqueous effluent from pulp mill or paper mill production is determined, and the obtained TOC value is quantitatively related to selected parts of the spectral information, obtained from the effluent.

10. The method of claim 7, wherein the organic content, defined as biological oxygen demand (BOD), in the aqueous effluent from pulp mill or paper mill production is determined, and the obtained BOD value is quantitatively related to selected parts of the spectral information, obtained from the effluent.

11. The method of claim 7, wherein the organic content, defined as absorbable organic halogenates (AOX), in the aqueous effluent from pulp mill or paper mill production is determined, and the obtained AOX value is quantitatively related to selected parts of the spectral information, obtained from the effluent.

12. The method of claim 7, wherein the organic content, defined as one or several groups related to their chemical structures is determined.

13. The method of claim 7, wherein the suspended solids in the aqueous effluent from pulp mill or paper mill production is determined, and the value of suspended solids is quantitatively related to selected parts of the spectral information, obtained from the effluent.

14. The method of claim 7, wherein the colour in the aqueous effluent from pulp mill or paper mill production is determined, and the COD value is quantitatively related to selected parts of the spectral information, obtained from the effluent.

15. The method of claim 7, wherein the wash losses, defined as chemical oxygen demand (COD) or sodium sulphate, in the aqueous effluent from pulp mill or paper mill production is determined, and the wash losses are quantitatively related to selected parts of the spectral information, obtained by measuring the effluent.

16. The method of claim 1, wherein the principal components are calculated and the values as obtained are related as a function of time to known qualitative or quantitative parameters used for process control.

* * * * *